(12) United States Patent
Jarvis

(10) Patent No.: US 8,308,860 B2
(45) Date of Patent: Nov. 13, 2012

(54) LASER-MARKABLE COMPOSITIONS

(75) Inventor: Anthony N Jarvis, Widnes (GB)

(73) Assignee: Datalase Ltd., Cheshire (GB)

( * ) Notice: Subject to any disclaimer, the term of this patent is extended or adjusted under 35 U.S.C. 154(b) by 292 days.

(21) Appl. No.: 12/443,769

(22) PCT Filed: Oct. 19, 2007

(86) PCT No.: PCT/GB2007/050647
§ 371 (c)(1),
(2), (4) Date: Mar. 31, 2009

(87) PCT Pub. No.: WO2008/050153
PCT Pub. Date: May 2, 2008

(65) Prior Publication Data
US 2010/0068234 A1    Mar. 18, 2010

(30) Foreign Application Priority Data
Oct. 27, 2006  (GB) .................................. 0621475.3

(51) Int. Cl.
*C09D 11/00* (2006.01)
(52) U.S. Cl. ................. 106/31.32; 106/31.64; 106/31.16
(58) Field of Classification Search ............... 106/31.32, 106/31.64, 31.16
See application file for complete search history.

(56) References Cited

U.S. PATENT DOCUMENTS

| 5,627,014 A | 5/1997 | Chu et al. | |
|---|---|---|---|
| 6,261,348 B1* | 7/2001 | Kwan et al. | 106/31.14 |
| 2005/0053863 A1* | 3/2005 | Gore | 430/270.14 |
| 2005/0164116 A1* | 7/2005 | Wang et al. | 430/138 |
| 2005/0231585 A1* | 10/2005 | Mudigonda et al. | 347/238 |
| 2007/0277700 A1* | 12/2007 | Wagenblast et al. | 106/31.45 |
| 2010/0018957 A1* | 1/2010 | Khan | 219/121.85 |
| 2011/0148092 A1* | 6/2011 | Jarvis et al. | 283/67 |
| 2011/0151380 A1* | 6/2011 | Jarvis et al. | 430/270.11 |
| 2011/0151384 A1* | 6/2011 | Walker et al. | 430/338 |
| 2011/0159268 A1* | 6/2011 | Jarvis | 428/221 |

FOREIGN PATENT DOCUMENTS

| EP | 0 558 078 | 9/1993 |
|---|---|---|
| WO | WO 02/074548 | 9/2002 |
| WO | WO 2004/043704 | 5/2004 |
| WO | WO 2005/012442 | 2/2005 |
| WO | WO 2005/068207 | 7/2005 |
| WO | WO 2005085372 A1 * | 9/2005 |
| WO | WO 2007/063332 | 6/2007 |

* cited by examiner

*Primary Examiner* — Melvin C Mayes
*Assistant Examiner* — Veronica F Faison
(74) *Attorney, Agent, or Firm* — Saliwanchik, Lloyd & Eisenschenk

(57) ABSTRACT

A laser-markable composition comprises a marking component and an organic compound, wherein the organic compound absorbs laser radiation at 780 to 2000 nm and thereby causes the marking component to change color, and wherein the organic compound has an absorptivity ratio, A r, of at least 1.25, wherein the absorptivity ratio is defined as formula (I): wherein: $A_{p780-2000\ nm}$ is an absorbance peak in the wavelength region of 780 to 2000 nm; and $A_{ave600-700\ nm}$ is the average absorbance in the wavelength region of 400 to 700 nm.

$$A_y = \frac{A_{p780-2000\ nm}}{A_{ave400-700\ nm}} \qquad (I)$$

28 Claims, No Drawings

LASER-MARKABLE COMPOSITIONS

CROSS-REFERENCE TO A RELATED APPLICATION

This application is a National Stage Application of International Application Number PCT/GB2007/050647, filed Oct. 19, 2007; which claims priority to Great Britain Patent Application No. 0621475.3, filed Oct. 27, 2006; both of which are incorporated herein by reference in their entirety.

FIELD OF THE INVENTION

This invention relates to a laser-markable composition comprising a marking component and an organic compound, wherein the organic compound absorbs laser light and causes the marking component to change colour.

BACKGROUND OF THE INVENTION

It is well known that organic dyes which absorb laser light can be used to mark substrates via a burning or "charring" mechanism. The absorption superheats the substrate causing localised charring and thus a contrasting image to form. Charring, however, can be highly damaging to substrates and thus is not suitable in all applications.

U.S. Pat. No. 6,911,262 teaches the use of organic near infrared absorbing dyes in laser welding applications.

U.S. Pat. No. 5,627,014 and its prior art preamble teaches the use of organic near infrared absorbing dyes in the conversion of organic leuco dyes into coloured compounds.

WO05/012442 teaches the use of conductive organic polymers as NIR absorbers in laser marking applications. However, conductive polymers when supplied as solutions are usually quite dilute (<2% w/w, ie weight per weight) and thus inconvenient to formulate with. Making them more concentrated can lead to instability such as gelling and flocculation. Conductive polymers also need to be used at either high or low pH, again this reduces formulation flexibility. The overall consequence of all these factors is a limited shelf-life stability of final ink formulations containing conductive polymers. When supplied in solid form conductive polymers can be very difficult to dissolve/disperse which also makes them arduous to use in ink formulations. Conductive polymers also usually have considerable visible absorptivity which gives them an undesirable dark colouration to the eye.

SUMMARY OF THE INVENTION

This invention is based on the finding that an organic compound that absorbs radiation in the near infrared region (NIR) of the electromagnetic spectrum (i.e. 780 to 2000 nm), can give rise to contrasting images when incorporated in an AOM-based ink formulation and subjected to laser radiation in the NIR region.

According to one aspect, the invention provides a laser-markable composition comprising a marking component and an organic compound, wherein the organic compound absorbs laser irradiation at 780 to 2000 nm and thereby causes the marking component to change colour, and wherein the organic compound has an absorption peak in the wavelength region of 780 to 2000 nm, and wherein this absorption peak has an absorptivity ratio, $A_r$, of at least 1.25, wherein the absorptivity ratio is defined as $$A_r = \frac{A_{p780-2000\,nm}}{A_{ave400-700\,nm}}$$

wherein:
$A_{p780-2000\,nm}$ is an absorbance peak in the wavelength region of 780 to 2000 nm; and
$A_{ave400-700\,nm}$ is the average absorbance in the wavelength region of 400 to 700 nm.

According to other aspects, the invention provides a substrate coated with this composition, an ink formulation comprising this composition, and a method for forming an image on a substrate, wherein the method comprises applying on to the substrate the composition of the invention and irradiating the substrate with a laser.

DETAILED DESCRIPTION

An organic compound is defined as one which contains at least one carbon atom covalently bonded to at least one hydrogen atom. The organic compounds of the present invention generally have a molecular mass of less than 2500 g/mol and preclude chain type molecules consisting of structural units and a large number of repeating subunits connected by covalent chemical bonds (i.e. polymers).

The organic compounds of the present invention typically have an absorptivity ratio ($A_r$) of at least 1.25, preferably 2, more preferably still 3, and much more preferably still 5. The absorptivity ratio, $A_r$, is defined as:

$$A_r = \frac{A_{p780-2000\,nm}}{A_{ave400-700\,nm}}$$

wherein:
$A_{p780-2000\,nm}$ is an absorbance peak in the wavelength region of 780 to 2000 nm, and
$A_{ave400-700\,nm}$ is the average absorbance in the wavelength region of 400 to 700 nm.

Preferably the absorption peak in the wavelength region of 780 to 2000 nm is the maximum absorption peak in this wavelength region, i.e. the largest magnitude peak exhibited at any wavelength in this region. Most preferably the absorption peak in the wavelength region of 780 to 2000 nm is the maximum absorption peak across all wavelengths.

The $A_r$ of a given organic compound can be determined by dissolving it in a suitable solvent and then using an appropriate spectrophotometer to measure the absorbance in the region 400 to 2000 nm at 1 nm intervals. Alternatively, the $A_r$ of a given organic compound can be determined via the absorptivity properties of a resultant drawdown of an ink containing said organic compound. An absorbance peak in the region 780 to 2000 nm can then be easily identified, particularly if it is the maximum absorbance peak in this region or across all wavelengths. The average (mean) absorbance in the region 400 to 700 nm can then easily be determined ($A_{ave400\,to700\,nm}$):

$$A_{ave400-700\,nm} = \frac{Abs_{400to700\,nm}}{n}$$

wherein:
$Abs_{400-700\,nm}$ is the sum of the absorbance from 400 to 700 nm in 1 nm intervals; and n is the number of discrete wavelength measurements (ie. 300 in this case).

The organic compounds of the present invention can comprise, but are not limited to, non-polymeric substances also known to those skilled in the art as near infrared dyes or pigments. Without being limited by theory, it is believed that the compounds of the present invention absorb NIR radiation by an electronic excitation mechanism (such as, $\pi,\pi^*$) rather than a vibrational excitation mechanism.

The organic compounds can be selected from, but are not limited to, metallo-porphyrins, metallo-thiolenes, metallo-polythiolenes, metallo-phthalocyanines, aza-variants or annellated variants of any of these, pyrylium salts, squaryliums, croconiums, amminiums, diimoniums, cyanines and indolenine cyanines.

Examples of organic compounds that can be used in the present invention are taught in U.S. Pat. No. 6,911,262, and are given in Developments in the Chemistry and Technology of Organic dyes, J Griffiths (ed), Oxford: Blackwell Scientific, 1984, and Infrared Absorbing Dyes, M Matsuoka (ed), New York: Plenum Press, 1990. Further examples of the NIR dyes or pigments of the present invention can be found in the Epolight™ series supplied by Epolin, Newark, N.J., USA; the ADS series supplied by American Dye Source Inc, Quebec, Canada; the SDA and SDB series supplied by HW Sands, Jupiter, Fla., USA; the Lumogen™ seJies supplied by BASF, Germany, particularly Lumogen™ IR765, IR788 and IR 1055; the Pro-Jet™ series of dyes supplied by FujiFilm Imaging Colorants, Blackley, Manchester, UK, particularly Pro-Jet™ 830NP, 900NP, 825LDI and 83OLDI; the Filtron™ series supplied by Gentex Corporation of Simpson, Pa., USA and those supplied by Organica Feinchemie GmbH of Wolfen, Germany.

The organic compounds of the present invention can be non-ionic, cationic, anionic or zwitterionic in character. They can be water-soluble or dispersible, or solvent-soluble or dispersible.

Particularly preferred examples of organic compounds are those that have minimal visible light absorptivity and thus when incorporated into an ink formulation and drawn down on to a substrate appear colourless or virtually colourless to the eye. However, the dye can also appear coloured thus making them suitable for use on substrates which have a similar colour to the dye. For example brown/beige dyes and pigments are particularly suitable for use on corrugate.

Particularly preferred compounds are also those that have an absorbance peak, especially a maximum absorbance peak (either maximum in the range 780-2000 nm or maximum across all wavelengths), at or close to the operating wavelength of the laser beam employed, preferably within ±50 nm of the operating wavelength.

The organic compounds of the invention are particularly advantageous over other NIR absorbers known to work with AOM such as copper (II) hydroxide phosphate (CHP) as they can surprisingly produce effects at relatively low concentrations, i.e. typically less than 5% w/w in a formulation, whereas CHP generally requires greater than 20% w/w.

The invention utilises the organic compound as a functional IR-absorber/colour developer material which, on absorption of radiation from a laser source, can directly produce a colour-forming reaction when in combination with a component that will otherwise undergo the desired reaction on irradiation at a higher wavelength. For example, it can be used in combination with an oxymetal anion component in an applied coating, to generate a distinct coloured image. Alternatively, a colour-forming component is used, to generate a distinct image.

According to the present invention, the potential of utilizing fibre, diode, diode array and $CO_2$ lasers for imaging applications on, for example, packaging can be realized. It has been shown that, by the application of liquid film-forming inks which contain the composition of the invention onto various substrates to produce coatings capable of distinct colour change, exposure to near-IR sources produces good results.

The organic compound should preferably be compatible with the colour change chemistry, should preferably have no or minimal absorption in the visible region of the absorption spectrum, and should preferably be an efficient absorber of radiation at a wavelength of 780 to 2000 nm. Particularly preferred compounds are those that have an absorbance peak, especially a maximum absorbance peak (either maximum in the range 780-2000 nm or maximum across all wavelengths), at or close to the operating wavelength of the laser beam employed. It should preferably have thermally stability greater than 200° C. and good light stability and weatherability. It should preferably be colourless or impart minimal colour in the finished coating formulation. Further preferred features of the MR dye or pigment are that it should be water-stable, have minimal solubility in water, be compatible with water-based binders/compatible with common organic solvents, environmentally friendly, readily available and non-toxic.

Other than the organic compound, compositions of and for use in the present invention may comprise materials of the type described in the publications identified above. In one particular embodiment of the invention, when a poly-metal salt is used in combination with an additional marking component, then a composite colour can be achieved. The marking component may be one or more of a range of materials such as, for example, dye precursor, colour developer+dye precursor, oxy metal salt, oxy metal salt+dye precursor, oxy metal complex, or oxy metal complex+dye precursor. Other suitable components include pigment precursors. Any of all such components may be polymeric or halogenated; cellulosic materials or sugars may also be used. Examples of charrable polymers and sugars are polyvinyl alcohol, carboxymethylcellulose, hydroxypropylcellulose, fructose, glucose, sucrose and starch.

All such active materials described above can be supported on inert materials as alumina, titanium oxide, zinc oxide, kaolin or mica.

A preferred component for use in the invention is a compound including an oxymetal anion. In combination with a salt, this typically allows marking with a fibre, diode, diode array or $CO_2$ laser. A suitable oxymetal anion component may be one or more of a range of materials, for example, ammonium octamolybdate (AOM), bis[2-(ethylhexylamine)]molybdate or di(cyclohexylamine)molybdate. A suitable ink formulation comprises 10-50% w/w of this component.

A colour-forming component may be included. Such materials are well known to those of ordinary skill in the art. Examples of suitable colour-formers include one or more of a range of conventional materials such as electron-donating materials, e.g. phthalides, fluorans and leuco dyes, for example crystal violet lactone. Lewis acids, whether electron-accepting or acid-generating, may also be used; examples are hydroxybenzoate, bisphenol A, zinc stearate and others.

Compositions for use in the invention can be produced in solvent, non-solvent and solvent-less binder systems such as Tampoprinting inks, UV-curing inks etc. A suitable binder, which may be water-soluble, alkali-soluble or an emulsion polymer, examples being polyvinyl alcohol (available as Gohsenol GH-17), acrylic emulsion (available from Scott Bader as Texicryl 13-011), materials available as Ineos Elvacite 2013, 2028, 2043 or 30, polyvinyl butyral (available as Pioloform) and nitrocellulose, e.g. in an amount of 10-50% w/w.

Pigments such as fumed silica or zinc stearate may also be used, e.g. in an amount of 10-50% w/w. Other materials that may be used include any one or more of antioxidants, reducing agents, lubricating agents, surfactants, pigments, sensitizers and defoamers.

When formulated as an ink for use in the invention, e.g. as a solution, dispersion or suspension, a suitable carrier liquid or solvent may be aqueous or organic, and other components will be chosen accordingly. For example, the liquid may be or comprise water or an organic solvent such as isopropanol, methyl ethyl ketone, ethanol or ethyl acetate, optionally with amine and/or surfactant, e.g.

preferably in an amount of about 20-80% w/w. Compositions may be prepared by dispersion of components in water-based polymer binder solutions such as polyvinyl alcohol and film-forming emulsions such as acrylics. These compositions may be produced by using any of:

a) mechanical mixing, e.g. leading edge-trailing blade stirring b) ceramic ball grinding and milling c) silverson mixing d) glass bead mechanical milling, e.g. in an Eiger Torrance motormill e) Ultra Turrax homogeniser f) mortar and pestle grinding By application of liquid film-forming inks onto various substrates, coatings capable of distinct colour change can be produced. Exposure to near-IR sources can produce dramatically different results, dependent primarily on the formulation of the ink. Due to effectiveness of the invention in producing a black image on exposure to fibre, diode or diode array laser wavelengths, e.g. when including a non-stoichiometric compound and an oxymetal anion, this may be further exploited by differentiating between activating sources.

A composition of or for use in the invention can be used to produce an IR-sensitive coating that can be applied by a range of methods such as flood-coating, flexo/gravure etc. The coating can be applied to a range of substrates such as paper, paperboard, flexible plastic film, corrugate board etc.

Further media that may be used in the invention are UV-curable flexographic inks, UV-curable offset inks, conventional offset inks, melt-extrudable polymer and powder coatings.

The following Examples illustrate the invention, but are not intended to be limiting in scope.

Example 1

MEK Based Ink

The following formulation was prepared:

25 g Elvacite 2028 (low molecular weight methacrylate copolymer, ex. Lucite International);

1 g of N,N,N',N'-tetrakis(4-dibutylaminophenyl)-p-benzoquinone bis(iminium hexa-fluoroantimonate), an NIR dye supplied by ADSdyes, Quebec, Canada, as ADS1065A;

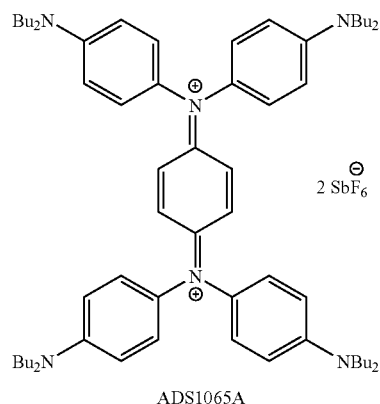

ADS1065A 25 g of ammonium octamolybdate (technical grade ex. Climax Molybdenum); and 49 g of methyl ethyl ketone (ACS reagent 99%, ex. Aldrich)

The formulation was Silverson mixed for 10 minutes prior to drawing down on to 50 micron PET film (ex. HiFi) at a coat weight of 4.0±1.0 gsm.

The absorbance spectrum of the draw down was measured from 200 to 2500 nm using a Varian Cary 5000 UV-VIS-NIR spectrometer connected to an IBM compatible pc. This data was used to determine the average absorptivity in the range 400 to 700 nm and the maximum absorptivity at the region 780 to 2000 nm.

Average absorptivity in the range 400 to 700 nm=0.186.
Maximum absorptivity in the range 780 to 2000 nm=1.035.
This corresponds to an $A_r$ (absorbance ratio) of 5.57.

Marking was performed using a 963 nm diode laser with a power output of 3.8 W, and a 1066 nm fibre laser with a power output of 3.65 W. Both lasers were fitted to a galvo scanning head and were used to create 1 cm² images at known times, and therefore known fluences, for optical density measurement. Optical density was measure using a Gregtag-MacBeth SpectroEye with $D_{65}$ illumination, 10° observer and black density measurement setting.

The fluence results were as follows for an optical density increase of 0.5:

| Laser wavelength | Fluence for OD = 0.5 Jcm$^{-2}$ |
|---|---|
| 963 nm | 2.6 |
| 1066 nm | 1.4 |

Example 2

Ethanol B/Ethyl Acetate Ink

The following formulation was prepared:
6.5 g of Pioloform BN-18, polyvinyl butyral resin, supplied by Wacker Polymer Systems;
1.8 g of Nitrocellulose grade DCX 3-5, supplied by Noble Enterprises;
2.3 g Casathane 920, plasticizing polyurethane, supplied by Thomas Swan & Co Ltd;
1 g of dibutyl sebacate, plasticizer, supplied by Eastman;
1.1 g of Vilosyn 339, alcohol soluble resin, supplied by VIL Resins;

1.7 g of Crayvallac WS-4700, an isopropanol-based polyethylene wax dispersion, supplied by Cray Valley;
54.6 g of ethanol and ethyl acetate solvents (3:1 mixture), standard laboratory grade;
30 g AOM; and
1.0 g ADS1065A.

The formulation was milled using an Eiger-Torrance bead mill (50 ml capacity) for 15 minutes prior to drawing down on to 50 micron PET film (ex. HiFi) at a coat weight of 4.0±1.0 gsm.
Average absorptivity in the range 400 to 700 nm=0.166.
Maximum absorptivity in the range 780 to 2000 nm=1.02.
This corresponds to an $A_r$ (absorption ratio) of 6.13.

The fluence results were as follows for an optical density increase of 0.5:

| Laser wavelength | Fluence for OD = 0.5 Jcm$^{-2}$ |
| --- | --- |
| 963 nm | 1.9 |
| 1066 nm | 1.3 |

The ink was then applied to the "card" type substrates: natural top liner and Smurfit-Stone kraft liner (42 pound) at a coat weight of 3.0±0.5 gsm.

Both coated substrates were then imaged using the 1066 nm fibre laser and in each case machine readable barcodes and human readable text was produced.

Example 3

Aqueous Ink

The following ink formulation was prepared:
37 g of UH-5000, an acrylic PU binder, supplied by Scott-Bader;
24 g of Glascol LS-2, a modified acrylic aqueous emulsion, supplied by CibaSC;
1 g of Dispelair CF-49, a defoamer, supplied by Blackburn Chemicals;
4 g of Glaswax E1, a PE wax emulsion, supplied by CibaSC;
2.5 g of Tyzor LA, a lactic acid titanate adhesion promoter, supplied by DuPont;
0.5 g of Aerosil 200, a fumed silica anti-setting agent, supplied by Degussa;
30 g AOM; and
1.0 g of Epolight™ 2164, a monovalent tris-amminium dye, supplied by Epolin, Newark, N.J., USA.

The formulation was milled using an Eiger-Torrance bead mill (50 ml capacity) for 15 minutes prior to drawing down on to 50 micron PET film (ex. HiFi) at a coat weight of 10.0±1.0 gsm.
Average absorptivity in the range 400 to 700 nm=0.146.
Maximum absorptivity in the range 780 to 2000 nm=0.391.
This corresponds to an $A_r$ (absorption ratio) of 2.68.

The fluence results were as follows for an optical density increase of 0.5:

| Laser wavelength | Fluence for OD = 0.5 Jcm$^{-2}$ |
| --- | --- |
| 963 nm | 3.0 |
| 1066 nm | 2.4 |

The ink was then applied to the "card" type substrates: natural top liner and Smurfit-Stone kraft liner (42 pound) at a coat weight of 3.0±0.5 gsm.

Both coated substrates were then imaged using the 1066 nm fibre laser and in each case machine readable barcodes and human readable text was produced.

Examples 4 and 5

The ethanol B/ethyl acetate ink formulation as described in example 2 was prepared but replacing ADS1065A with:
Example 4: SDA 9158 supplied by HW Sands Corp (1 g).
Example 5: SDA 9800 supplied by HW Sands Corp (1 g).

The resultant inks were applied to multiply polyethylene based film at a coat weight of 10±1 gsm.

Example 4

Average absorptivity in the range 400 to 700 nm=0.101.
Maximum absorptivity in the range 780 to 2000 nm=0.898
This corresponds to an $A_r$ (absorbance ratio)=8.9.

Example 5

Average absorptivity in the range 400 to 700 nm=0.151.
Maximum absorptivity in the range 780 to 2000 nm=0.912
This corresponds to an $A_r$ (absorbance ratio)=6.0.

Example 4 was marked using an individually addressed diode array laser system operating at a wavelength of 808 nm. Example 5 was marked using an individually addressed diode array laser system operating at a wavelength of 98 nm. In both cases, readable text characters were generated.

The invention claimed is:

1. A laser-markable composition comprising a marking component and an organic compound, wherein the marking component is a molybdate, wherein the organic compound is a near infrared-absorbing dye or pigment, and wherein the organic compound absorbs laser radiation at 780 to 2000 nm and thereby causes the marking component to change colour, and wherein the organic compound has an absorptivity ratio, $A_r$, of at least 1.25, wherein the absorptivity ratio is defined as:

$$A_r = \frac{A_{p780-2000\ nm}}{A_{ave400-700\ nm}}$$

wherein:
$A_{p780-2000\ nm}$ is an absorbance peak in the wavelength region of 780 to 2000 nm; and
$A_{ave400-700\ nm}$ is the average absorbance in the wavelength region of 400 to 700 nm.

2. The composition according to claim 1, wherein the marking component in the absence of the organic compound undergoes a colour change in response to laser irradiation at a wavelength above 2000 nm but not between 780-2000 nm.

3. The composition according to claim 1, wherein the organic compound has an absorptivity ratio, $A_r$, of at least 2.

4. The composition according to claim 3, wherein $A_r$ is at least 3.

5. The composition according to claim 3, wherein $A_r$ is at least 5.

6. The composition according to claim 1, wherein the absorption peak is the maximum absorption peak across all wavelength regions.

7. The composition according to claim 1, wherein the organic compound has a molecular mass less than 2500 g/mol.

8. The composition according to claim 1, wherein the organic compound absorbs near infrared radiation by an electronic absorption mechanism.

9. The composition according to claim 1, wherein the organic compound is selected from a metallo-porphyrin, a metallo-thiolene, a polythiolene, a metallo-phthalocyanine, an aza-variant or annellated variant of any of these, a pyrylium, a squarylium, a croconium, an amminium, a diimonium, a cyanine or an indolenine cyanine.

10. The composition according to claim 9, wherein the organic compound is non-ionic, cationic, anionic or zwitterionic.

11. The composition according to claim 9, wherein the organic compound is water-soluble or dispersible, or solvent-soluble or dispersible.

12. The composition according to claim 1, wherein the organic compound is solvent-dispersible such that it disperses within the composition.

13. The composition according to claim 1, wherein the composition is essentially colorless.

14. The composition according to claim 1, wherein the marking component is an octamolybdate.

15. The composition according to claim 14, wherein the marking component is ammonium octamolybdate.

16. The composition according to claim 1, wherein the composition additionally comprises a colour-forming compound.

17. The composition according to claim 1, wherein the composition additionally comprises a binder.

18. The composition according to claim 1, wherein the composition is water-based.

19. The composition according to claim 1, wherein the composition comprises an organic solvent.

20. An ink formulation comprising the composition of claim 1.

21. A substrate coated with a composition according to claim 1.

22. The substrate according to claim 21, wherein the substrate comprises paper, cardboard, plastic, textile, wood, metal, glass, leather, foodstuff or a pharmaceutical composition.

23. A method for forming an image on a substrate, wherein the method comprises applying onto the substrate a composition according to claim 1, and irradiating the substrate with a laser.

24. The method according to claim 23, wherein the laser is selected from a fibre, diode, diode array or $CO_2$ laser.

25. The method according to claim 23, wherein the laser has an operating wavelength in the range of 780 to 2000 nm.

26. The method according to claim 23, wherein the substrate is coated with the composition.

27. The method according to claim 23, wherein the organic compound is solvent-dispersible such that it disperses within the composition.

28. The method according to claim 23, wherein the composition is essentially colorless.

* * * * *